(12) United States Patent
Pontecorvo et al.

(10) Patent No.: US 11,607,528 B2
(45) Date of Patent: Mar. 21, 2023

(54) SUBCUTANEOUS FIXING SYSTEM FOR MEDICAL DEVICES

(71) Applicant: Servimed Industrial S.p.A., Rome (IT)

(72) Inventors: Carmine Pontecorvo, Capri (IT); Luca Del Regno, Montoro (IT)

(73) Assignee: SERVIMED INDUSTRIAL S.P.A., Rome (IT)

( * ) Notice: Subject to any disclaimer, the term of this patent is extended or adjusted under 35 U.S.C. 154(b) by 36 days.

(21) Appl. No.: 17/512,295

(22) Filed: Oct. 27, 2021

(65) Prior Publication Data

US 2022/0062593 A1    Mar. 3, 2022

Related U.S. Application Data

(63) Continuation of application No. PCT/IB2021/053331, filed on Apr. 22, 2021.

(30) Foreign Application Priority Data

Apr. 22, 2020 (IT) .................. 102020000008623

(51) Int. Cl.
*A61M 25/01* (2006.01)
*A61M 25/02* (2006.01)
*A61M 39/02* (2006.01)
*A61M 39/24* (2006.01)

(52) U.S. Cl.
CPC ..... *A61M 25/02* (2013.01); *A61M 2025/0273* (2013.01); *A61M 2025/0286* (2013.01); *A61M 2039/0223* (2013.01); *A61M 2039/0273* (2013.01); *A61M 2039/0279* (2013.01); *A61M 2039/244* (2013.01); *A61M 2039/2466* (2013.01)

(58) Field of Classification Search
CPC .... A61M 2039/244; A61M 2039/2466; A61M 2039/0223; A61M 2039/0273; A61M 2039/0279; A61M 2025/0286; A61M 2025/0273; A61M 2025/0278; A61M 25/02
See application file for complete search history.

(56) References Cited

U.S. PATENT DOCUMENTS

| 5,571,137 A * | 11/1996 | Marlow ............... A61B 17/29 606/205 |
| 2012/0078191 A1 | 3/2012 | Rosenberg et al. |
| 2014/0107584 A1 | 4/2014 | Rosenberg et al. |
| 2014/0228810 A1 | 8/2014 | Rosenberg et al. |
| 2014/0330247 A1 | 11/2014 | Rosenberg et al. |

OTHER PUBLICATIONS

International Search Report and Written Opinion for Corresponding International Application No. PCT/IB2021/053331 (15 Pages) (dated Sep. 6, 2021).

* cited by examiner

*Primary Examiner* — Rebecca E Eisenberg
*Assistant Examiner* — Tania Ismail
(74) *Attorney, Agent, or Firm* — Lucas & Mercanti, LLP

(57) ABSTRACT

The present disclosure relates to a subcutaneous fixation system for fixing medical devices, in particular catheters, and keeping them in position with respect to an access point on the skin of a patient.

11 Claims, 5 Drawing Sheets

SUBCUTANEOUS FIXING SYSTEM FOR MEDICAL DEVICES

CROSS-REFERENCE TO RELATED APPLICATIONS

This application is a continuation of PCT/IB2021/053331, filed Apr. 22, 2021, which claims the benefit of Italian Patent Application No. 102020000008623, filed Apr. 22, 2020, the contents of each of which are incorporated herein by reference.

TECHNICAL FIELD

The present disclosure refers to a system for fixing or anchoring subcutaneously a medical device, for example, a catheter.

BACKGROUND OF THE INVENTION

The use of catheters such as venous, arterial or body fluid catheters is widely used in medical practice. Catheters may be used for dialysis, parenteral drug delivery, nutrition, hemodynamic monitoring, blood sampling, or body fluid drainage. In conventional practice, after being introduced, the catheter is fixed to the patient's skin using plasters, adhesives, tapes or bands. However, the removal of plasters, adhesives, tapes or bands may lead to displacement of the catheter as well as pain, hematoma and even bruising of the patient. In addition to this, all these fixing systems do not allow for proper monitoring of the area or proper hygiene and maintenance by health professionals. In addition, the repeated application of plasters on the catheter can lead to the formation of adhesive residues on its surface, facilitating the accumulation of contaminants and therefore the likelihood of infection at the insertion site. In cases where prolonged fixation is required, the catheter can be anchored by suturing the fitting, or other support, to the patient's skin. This obviously resulted in severe discomfort for patients.

The purpose of the present disclosure is thus to provide a fixing system that allows to keep a medical device, in particular a catheter, in the correct position, i.e. fixed with respect to the insertion or access site, for prolonged times, without causing the aforementioned drawbacks and, at the same time, to remove it easily when desired.

SUMMARY OF THE INVENTION

After extensive experimentation, a fixing system for medical devices, in particular catheters, has been developed, capable of anchoring said medical device not only by operating on the surface of the patient's skin, but also under the skin, preferably by exploiting the access site of the device itself.

Therefore, the object of the present disclosure is a subcutaneous fixing system for medical devices, in particular catheters, the essential characteristics of which are as defined in the attached claim 1. Other accessory technical characteristics are the subject of the dependent claims.

More particularly, the subject of the present disclosure is a subcutaneous fixing system for a medical device, which comprises a base stop (1) having a housing channel (c), configured to be reversibly coupled to the medical device, which extends substantially parallel to, or coincident with, its longitudinal axis (X); and an anchoring assembly (2) having a first arm (I) and a second arm (II) hinged together at an intermediate point (P), each of said first (I) and second (II) arms comprising a anchoring portion (a, a'), designed to unfold reversibly in a subcutaneous region with respect to an access point on the skin of a patient, and a connection portion (b, b'), operatively connected to the base stop (1) at a support point (s, s') on the proximal end of the base stop (1); wherein the base stop is reversibly foldable along a folding axis, parallel to or coinciding with said longitudinal axis, such that the anchoring portions of the first and second arm are substantially aligned along an access axis (A) when the base stop is in a folded configuration and substantially diverging with respect to the access axis (A) when the base stop is in the deployed configuration.

Another object of the present disclosure is a method for subcutaneous attachment of a medical device, for example a catheter, to the body of a patient by means of the attachment system according to any of the embodiments described below. In particular, the method may comprise: bending the base stop (1) downwards along a folding axis, parallel to or coincident with its longitudinal axis (X), so that the anchoring portions (a, a') of the first and second arms (I, II) are substantially aligned along an access axis (A); inserting only the anchoring portions (a, a') into the access hole of a catheter operated on the skin of a patient; releasing the base stop so that the anchoring portions (a, a') of the first and second arm (I, II) are substantially divergent with respect to said access axis (A); placing the catheter in the receiving channel (c) and if necessary securing the upper stop (3) on the base stop.

As will be evident to a person skilled in the art, the subcutaneous fixing system referred to in this disclosure guarantees a stable anchoring of the medical device, prevents its displacement thus avoiding interruptions in the administration of the therapy, allows both the view on the access site and the insertion of other devices or instruments in the site itself, allows to medicate the access site at 360° reducing the risk of infections and needs not to be replaced at scheduled intervals, but can be left in place for the entire duration of access.

Other aspects, characteristics and advantages of the anchoring system and method of the present disclosure will become evident from the detailed description given below.

BRIEF DESCRIPTION OF THE DRAWINGS

By way of example, with reference to the attached drawings, an embodiment of the subcutaneous fixing system of the present disclosure is presented, in which.

Figure 1:
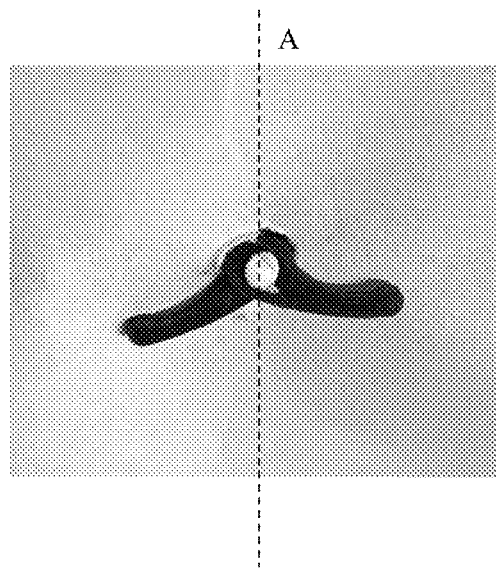
FIG. 1 is a perspective view of a subcutaneous fixing system according to an embodiment of the present disclosure, in which the base stop is in deployed configuration and therefore the anchoring portions (a, a') of the anchoring assembly (2) are deployed in a subcutaneous region, i.e. substantially diverging with respect to an access point on the skin of a patient.
Figure 2:
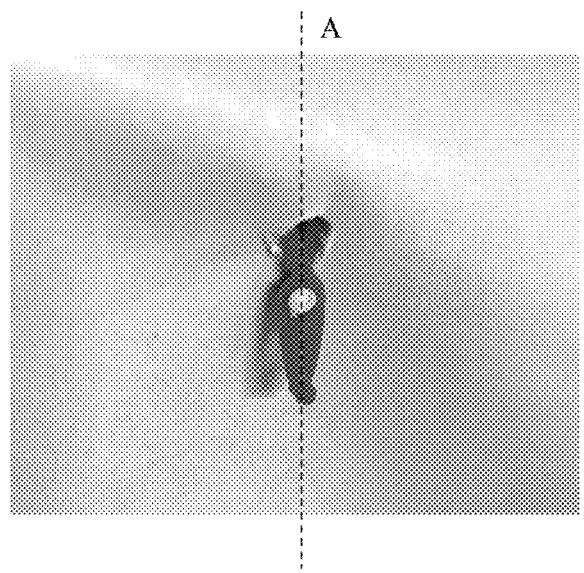
FIG. 2 is a perspective view of a subcutaneous fixing system according to an embodiment of the present disclosure, in which the base stop is in a folded configuration and therefore the anchoring portions (a, a') of the anchoring assembly (2) are substantially aligned along an access axis (A), perpendicular to an access point on the skin of a patient.
Figure 3:
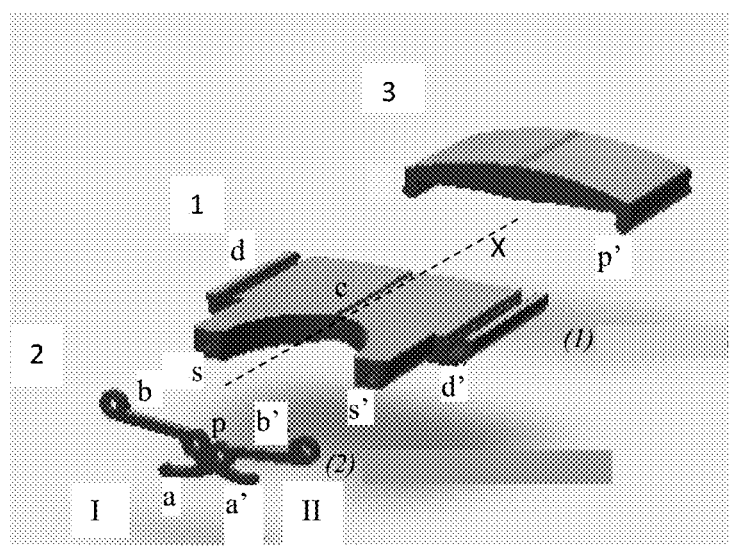
FIG. 3 is a perspective exploded view of the subcutaneous fixing system according to an embodiment of the present disclosure, in which the base stop (1), the anchor assembly (2) and the upper stop (3, optional) are depicted.
Figure 4:
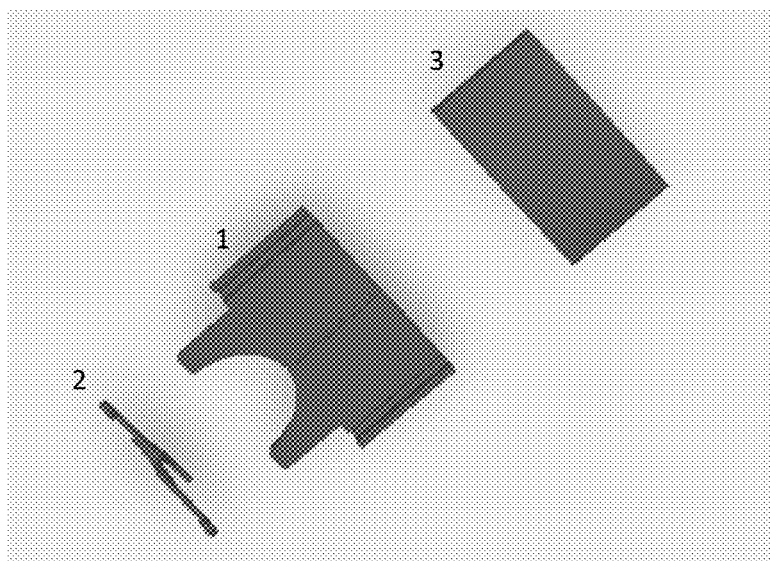
FIG. 4 is an exploded view from above of the fixing system according to an embodiment of the present disclosure.

The thicknesses and dimensions represented in the Figures introduced above are intended as purely illustrative, they are generally magnified and not necessarily shown in scale.

DETAILED DESCRIPTION OF PREFERRED EMBODIMENTS

Various embodiments and variants of the present disclosure will be described below, and this with reference to the figures introduced above. Similar components are labelled in the various figures with the same numerical reference.

In the detailed description that follows, further embodiments and variants with respect to embodiments and variants already treated in the same description will be illustrated limitedly to the differences with what has already been disclosed.

Furthermore, the various embodiments and variants described below are all capable of being used in combination, where compatible.

As anticipated above, a subcutaneous fixing system has been developed for a medical device capable of reversibly securing said device in position with respect to an access point on the skin of a patient. In the context of the present disclosure, the term "access point" is used interchangeably with "insertion point" and indicates the point of penetration of the medical device and/or of the present fixing system on the patient's skin.

In its simplest embodiment, the subcutaneous fixing system of the present disclosure comprises a base stop (1) having a planar main development and comprising a first face adapted to be placed on the skin of a patient and a second face, facing inwards opposite to the first face, suitable for receiving and housing a medical device or instrument. For this purpose, the second face of the base stop can be provided with a housing channel (c), which extends substantially parallel to or coincides with its longitudinal axis (X), suitable for receiving a medical device or instrument, such as a catheter. Said housing channel (c) can be, for example, a groove of a shape suitable for receiving, and thus retaining by friction, a medical device or a portion thereof external to the access point on the patient's skin. The housing channel can be of any shape suitable for receiving and holding the medical device or a portion thereof. By way of example, but in no limiting way, the housing channel may have a semicircular, circular or non-circular cross section, equal or different to the cross section of the device, or its portion, with which it is coupled. It is evident that the dimensions of the housing channel can be adapted to the type of device to be fixed so as to provide a secure coupling by friction, but without it being necessary to excessively compress the device to accommodate it or exert excessive traction to remove it.

Indicatively, the dimensions of the housing channel are equal to or lower, preferably 5-20% lower, than the dimensions of the medical device, or its portion, to be fixed. For example, given an 18 French gauge catheter (1 Ch=⅓ of mm), i.e. having an external diameter of 6 mm, the width of the groove could be equal to 4.8-6 mm. As will be evident to the expert in the field, the dimensions of the housing channel are not an essential feature but may be modified according to the selected material.

By way of example, the base stop (1) can be made of material suitable for allowing its elastic deformation, for example of a synthetic or natural polymer as defined below.

The base stop (1) may further comprise a folding axis substantially parallel to, or coincident with, its longitudinal axis (X) which extends from a proximal portion to a distal portion of the base stop. Preferably, the groove which acts as a housing channel (c) in the base stop (1) also performs the function of a folding axis since the elastic resistance opposed by the material forming the base stop will obviously be lower along said groove. The folding axis is a preferred, but not essential, feature of the fixing system referred to in this disclosure, which allows to guide in a controlled manner the transition from deployed configuration to folded configuration of the base stop. In fact, assuming, for example, that the folding axis coincides with the longitudinal axis (X), by pressing the two lateral ends of the base stop downwards, it will fold back on itself in a specular way (book-like) and then return to its unfolded, substantially planar conformation as soon as the two lateral ends are released.

The fixing system can further comprise an anchoring assembly (2) comprising a first arm (I) and a second arm (II) hinged together at an intermediate point (P). The arms may be hinged to each other according to any of the methods known in the art, for example, by means of a hinge, joint or revolving hinge. Each of said first (I) and second (II) arms can comprise an anchoring portion (a, a'), the portion that goes from the free end of each arm to the point P, capable of reversibly unfolding in a subcutaneous region with respect to an access point on the skin of a patient, and a connection portion (b, b') which extends from the point P to the opposite end, operatively connected to the base stop (1). The connection portions (b, b") of each of said first (I) and second (II) arms are operatively connected, or hinged, on the proximal end of the base stop (1) at respective support points (s, s').

The figures show that the first support point (s) of the first arm (I) and the second support point (s') of the second arm (II) are arranged on opposite sides with respect to the folding axis symmetrically at a distance from it. Thanks to this arrangement, when the base stop (1) is folded on itself along the folding axis to assume a folded configuration (FIGS. 5a and 5b), the connection portions (b, b') close like a scissor and the intermediate point (P) is moved away from said folding axis.

The fact that the P point moves away from the folding axis makes it easier to insert and remove the base stop. When the anchoring portions (a, a') are under the patient's skin and the base stop 1 must be removed, the intermediate point (P) is kept in contact with the patient's skin and the long base stop 1 is folded the folding axis. As it bends along the fold axis, the base stop 1 rises from the patient's skin because the midpoint (P) must move away from the fold axis. As a result, the base stop 1 may be folded without pinching the patient's skin as well.

Figure 5A:
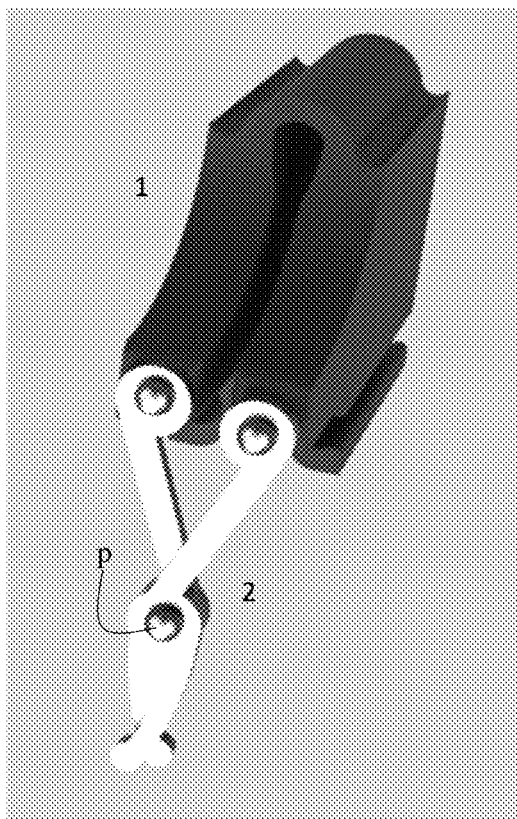
FIGS. 5a and 5b are perspective views of the base stop folded on itself along the folding axis and of the anchoring assembly with the connection portions b-b' closed like a scissor and with the intermediate point P moved away from the folding axis.
Figure 5B:
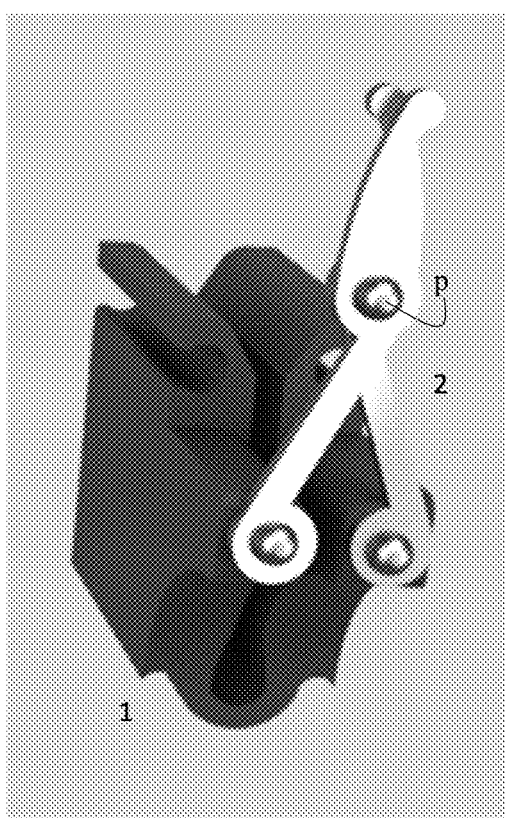
Figure 6A:
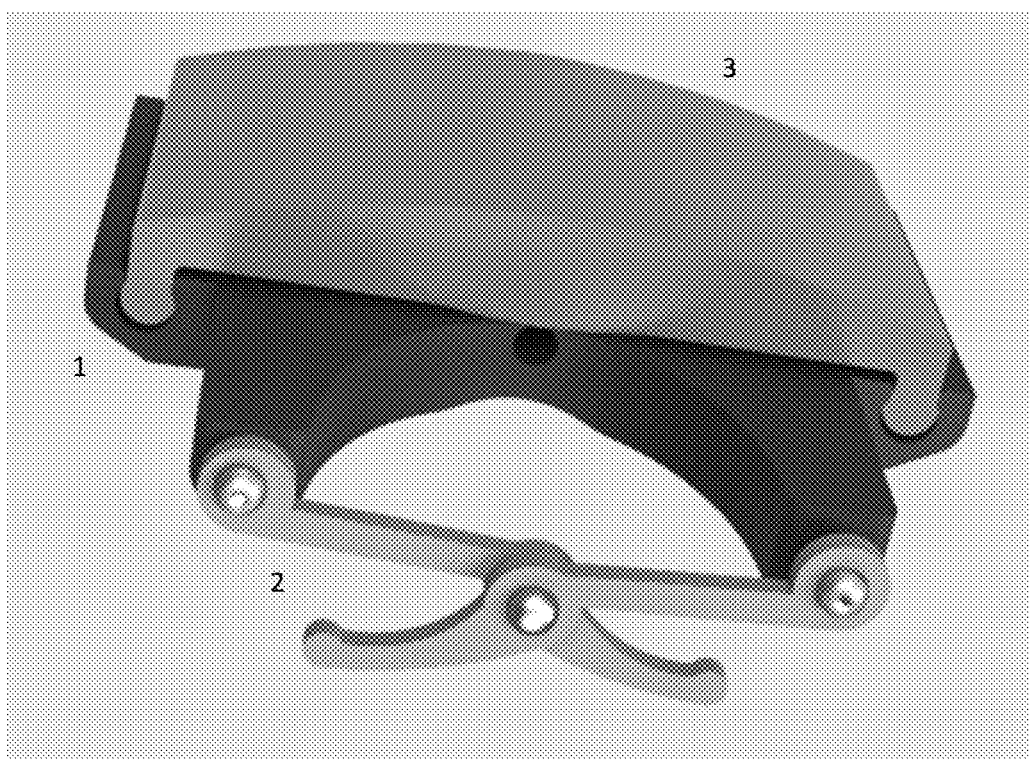
FIGS. 6a and 6b are perspective views of a subcutaneous fixing system according to the present disclosure with a medical device 3 fixed to the base stop 1.
Figure 6B:
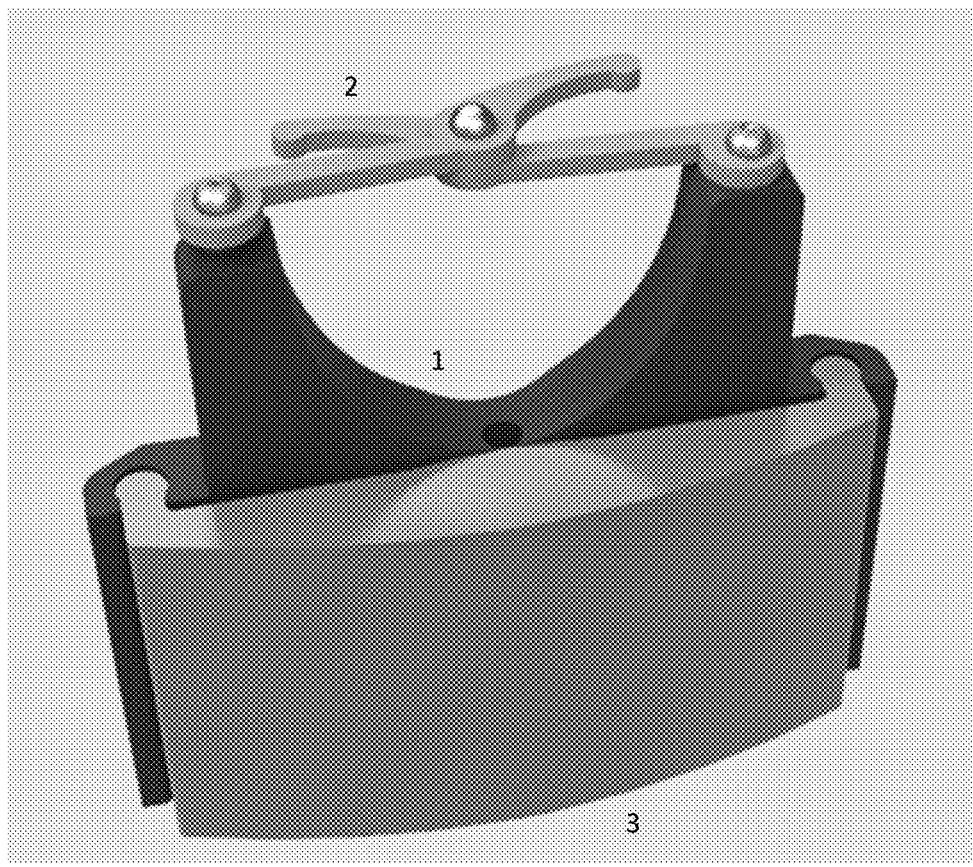

In the embodiment shown in FIGS. 5a and 5b the connecting portions (b, b') are arranged so that, when they close like scissors, they move the intermediate point (P) away from the folding axis, making it move substantially perpendicular to the folding axis. Consequently, by keeping the midpoint (P) in contact with the patient's skin and bending the base stop 1 along the fold axis, the base stop 1 lifts from the patient's skin moving perpendicular to the fold line. This makes it very easy to remove the base stop 1 because the anchoring portions (a, a'), which are under the patient's skin, are made to rotate only along their axis of rotation for the intermediate point (P) and it is not necessary to make transverse movements to detach the base stop 1 from the patient's skin.

The arms can be operatively connected, or hinged, to the base stop according to any of the methods known in the art as long as the arms are free to move with respect to the stop.

It will be evident to a skilled person that the subcutaneous fixing system of the present disclosure allows, by operating on the movement of the base stop (1) as described above, to control the movement of the anchoring assembly and in particular that of the anchoring portions (a, a') henceforth also called prongs.

Therefore, the present disclosure relates to a fixing system comprising a base stop (1) having a housing channel (c), configured to reversibly couple to the medical device, extending substantially parallel to its longitudinal axis (X); and an anchoring assembly (2) having a first arm (I) and a second arm (II) hinged together at an intermediate point (P), each of said first (I) and second (II) arms comprising an anchoring portion (a, a'), designed to unfold reversibly in a subcutaneous region with respect to an access point on the skin of a patient, and a connection portion (b, b'), operatively connected to the base stop (1) at a support point (s, s') on the proximal end of the base stop (1); wherein the base stop is reversibly foldable along a folding axis, parallel to or coinciding with said longitudinal axis; such that the anchoring portions of the first and second arm are substantially aligned along an access axis (A) when the base stop is in a folded configuration and substantially diverging with respect to the access axis (A) when the base stop is in the deployed configuration;

wherein the first support point (s) of the first arm (I) and the second support point (s') of the second arm (II) are arranged on opposite sides with respect to the folding axis symmetrically at a distance therefrom; and wherein the support points (s, s') and the first (I) and second (II) arms are configured so that, when the base stop (1) is folded back on itself along the folding axis to assume the folded configuration, the connecting portions (b, b') close like a scissor and the intermediate point (P) is moved away from the folding axis, preferably moving in a direction substantially perpendicular to the folding axis itself.

In the context of the present disclosure, the term "access axis (A)" means the insertion axis of the fixing system, in particular of the anchoring portions (a, a'), substantially perpendicular to an access point on the skin of a patient. As can be appreciated from the Figures, the plane in which the base stop (1) lies can be substantially perpendicular to the plane in which the anchor assembly (2) lies.

The system of the present disclosure may be used to secure medical devices of various kinds to a patient's body with respect to an access point operated on the patient's skin. The medical device can be selected from the group consisting of, but not limited to: catheter, probe, cannula and syringe.

The anchoring portions (a, a') of each of said first arms (I) and (II) of the anchoring assembly may have different shape, for example, shaped as a L, as a S, straight or arched. Preferably, the anchoring portions (a, a') are arched as this conformation guarantees a good seal and, at the same time, reduces the risk of subcutaneous injuries. In order to allow a good view of the access site, as well as any further access to the insertion site, the base stop (1) may optionally include a cavity. This cavity may have any type of shape as long as it guarantees the view on and/or access to the advert site. By way of example, hut in no limiting way, the cavity may have a circular, ellipsoidal, triangular, rectangular, or similar section.

Preferably, the cavity extends from the proximal to the distal portion of the base stop and, in particular, from the support points (s, s') for a portion (x) of the length (L) of the base stop.

Furthermore, the fixing system of the present disclosure may optionally also comprise an upper stop (3) adapted to be coupled to the base stop (1), giving greater stability to the fixing system, as well as further securing the medical device in position. For this purpose, the base stop (1) and the upper stop (3) may be respectively equipped with one or more coupling means conventionally known in the art, for example, those of the "male/female" type such as pin/hole, protrusion/groove and the like. By way of example, but in no way limiting, said upper stop (2) may have a first and a second lateral protrusion (p, p'), able to couple reversibly with a first and a second lateral groove (d, d') on the base stop (1), or vice versa.

In particular, each of said lateral protrusions can include an enlarged free end, that is, having a cross section greater than the cross section of the end constrained to the stop, capable of being wedged in the lateral grooves, deforming them elastically. By placing said protrusions in correspondence with said grooves, a user can elastically deform the mouth of the grooves simply by pressing the free ends of the protrusions against the mouth of the grooves and then secure the upper stop to the base one. Once the enlarged free end of the protrusion has crossed the mouth of a groove, the latter returns elastically to its original shape. The protrusion will not be able to spontaneously come out of the groove because the force required to bring out the enlarged end of the protrusion from the groove is greater than that which catheters implanted on patients are generally subjected to.

Furthermore, each of said lateral grooves can comprise an enlarged groove, i.e. having a cross section greater than the cross section of the mouth such that, once the coupling between the base stop and the upper stop has occurred, the upper stop can slide freely in the grooves only in the direction of the longitudinal axis (X) but cannot slide in a transverse direction or, as explained above, come out of the mouth of the groove without the user uncoupling the two stops. This represents a further advantage of the present disclosure because, should the upper stop obscure or obstruct the access site, it would always be possible to retract it by sliding it longitudinally in the opposite direction with respect to the access site.

The upper stop 3 can have a length l equal to, shorter or longer than the length L of the base stop (1). However, when the base stop includes the presence of the cavity, it is preferable that the upper stop has length l equal to or less than L x, where x is the depth of said cavity, so that, when applied on the base stop 1, the upper stop 3 does not cover said cavity or prevents access to the insertion site.

The base stop (1), the anchor assembly (2) and the upper stop (3) may be made of any biocompatible material, such as a polymeric or metallic material. Suitable polymeric materials may be selected from natural or synthetic polymers preferably selected from the group comprising, but not limited to, the following: polyglycolic acid (PGA), polylactic acid (PLA), polyethylene (PE), polypropylene (PP), polyethylene terephthalate (PET), polymethyl methacrylate (PMMA), polytetrafluoroethylene (PTFE), polyurethanes (PURs), polyvinyl chloride (PVC), silicones or mixtures of these. Suitable metallic materials may be selected from the group including, but not limited to, the following: titanium and its alloys, steels, cobalt and its alloys.

The base stop (1), the anchor assembly (2) and the upper stop (3) may be made of the same or different material, preferably chosen from the polymeric and metallic materials defined above. Therefore, the base stop (1), the anchor assembly (2) and the upper stop (3) may be made of a material independently selected from the group including, but not limited to: polyglycolic acid (PGA), polylactic acid (PLA), polyethylene (PE), polypropylene (PP), polyethylene terephthalate (PET), polymethyl methacrylate (PMMA), polytetrafluoroethylene (PTFE), polyurethanes (PURs), polyvinyl chloride (PVC), silicones, titanium and its alloys, steels, cobalt and its alloys, and mixtures of these.

The components of the fixing system may be prepared according to any of the methods known in the art as suitable for processing the aforementioned plastic or metal materials, for example, by means of injection molding, compression molding, casting molding. 3D molding, die casting techniques, thermoforming, or other processes for forming small plastic and/or metal objects for medical use.

An object of the present disclosure is also a method for the subcutaneous fixing of a catheter to the body of a patient by means of the fixing system according to any of the embodiments described up to now which comprises: —bending the base stop (1) downwards along a folding axis, parallel to or coinciding with its longitudinal axis (X), so that the anchoring portions (a, a') of the first and second arm (I, II) are substantially aligned along an access axis (A); inserting only the anchoring portions (a, a') into the access hole of a catheter operated on the skin of a patient; releasing the base stop so that the anchoring portions (a, a') of the first and second arm (I, II) are substantially divergent with respect to said access axis (A); placing the catheter in the receiving channel (c) and, if necessary, securing the upper stop on the base stop.

Preferably, the method uses as the access site the insertion site of the medical device itself, for example, of a catheter. The catheter will be positioned according to the conventional protocols in use in medical practice, letting the catheter escape outside the insertion site. After positioning the catheter, it will be sufficient to bring the fixing system of the present disclosure closer to the access site keeping the anchor assembly (2) in a position substantially perpendicular to the access site and folding the base stop (1) downwards until that the anchoring prongs (a, a') do not align along the access axis (A). Slightly lifting the catheter to locate the access site, inserting only the anchoring prongs following the subcutaneous path of the catheter, releasing the base stop to allow return to the substantially planar deployed configuration and laying the base stop on the patient's skin.

At this point, it will be possible to align the external portion of the catheter with the housing channel (c) on the base stop and insert it by applying light pressure. To increase the tightness and safety of the fixing device, it is then possible to apply the upper stop (3) on the base stop so as to match the fixing means provided, for example, the grooves (d, d') on the stop and the protrusions (p, p') on the upper stop and then to press to secure the upper stop to the base stop.

The fixing system according to any one of the embodiments described up to now has the advantage of allowing to anchor medical devices of various kinds to the skin of a patient, in a stable and safe way, without having to resort to adhesives or sutures. In particular, the subcutaneous anchoring assembly allows the medical device to be kept in position for the entire duration of the line or therapy, without the need to replace the fixing system in a programmed manner, not even for dressing and/or further access to the insertion site.

Advantageously, the fixing system of this disclosure, thanks to its extremely simple use, does not require the intervention of specialized medical personnel and may therefore be applied or removed even by the patient himself. In fact, the fixing system may be controlled using only one hand since, as described in detail above, by operating on the movement of the base stop it is possible to control the movement of the anchoring portion: by pressing down the lateral ends of the base stop, the anchor assembly will align along an access axis allowing the anchoring portions to be inserted into the access hole (folded system). By releasing the ends of the base stop, the anchoring portions will depart in a substantially perpendicular direction from the access axis, arranging themselves in a peripheral subcutaneous region with respect to the access site (system in unfolded configuration).

Another advantage of the fixing system is its ease of construction, since it may be made by molding plastic material to realize its individual components or accessories which are then easily assembled as described above.

The present disclosure has been set forth heretofore with reference to its preferred embodiments. It is to be understood that there may be other embodiments that refer to the same inventive core, all falling within the scope of the appended claims and/or in the points set out below.

The invention claimed is:

1. A subcutaneous fixing system for a medical device, comprising:
    a base stop having a housing channel, configured to be reversibly coupled to the medical device, which extends substantially parallel to, or coincident with, its longitudinal axis; and
    an anchor assembly having a first arm and a second arm hinged to each other at an intermediate point on said first and second arms, each of said first and second arms comprising an anchoring portion, apt to reversibly unfold in a subcutaneous region with respect to an access point on a patient's skin, and a connection portion, operatively connected to the base stop at a support point of a first support point and of a second support point on a proximal end of the base stop;
    wherein the base stop is reversibly foldable along a folding axis, parallel to or coincident with said longitudinal axis, such that the anchoring portions of the first and second arm are substantially aligned along an access axis when the base stop is in a folded configuration and substantially diverging from the access axis when the base stop is in a deployed configuration;
    wherein said first support point of the first arm and said second support point of the second arm are placed symmetrically at opposite sides in respect to said folding axis and at a distance therefrom; and
    wherein said support points and said first and second arms are configured so that, when the base stop is folded back on itself along the folding axis for assuming said folded configuration, said connection portions close like a scissor and said intermediate point is moved away from said folding axis.

2. The system of claim 1 wherein said medical device is a catheter, probe, cannula, or syringe.

3. The system according to claim 1, wherein the anchoring portions are arched.

4. The system according to claim 1, wherein a plane where the base stop lies is substantially perpendicular to the plane where the anchoring assembly lies.

5. The system according to claim 1, wherein said base stop further comprises a first and a second lateral groove.

6. The system according to claim 5, further comprising an upper stop having a first and second lateral protrusion, suitable for reversibly coupling with the lateral grooves of the base stop.

7. The system according to claim 1, wherein the base stop comprises a cavity which develops from the support points towards a distal portion for a segment (x) of the length (L) of the base stop.

8. The system according to claim 6, wherein the upper stop has a length equal to or less than L−x.

9. The system according to claim 6 wherein the base stop, the anchoring assembly and the upper stop are made of the same or different material.

10. The system according to claim 9 wherein the material for the base stop, the anchoring assembly and the upper stop are independently made of a member selected from the group consisting of: polyglycolic acid (PGA), polylactic acid (PLA), polyethylene (PE), polypropylene (PP), polyethylene terephthalate (PET), polymethyl methacrylate (PMMA), polytetrafluoroethylene (PTFE), polyurethanes (PURs), polyvinyl chloride (PVC), silicones, titanium and its alloys, steels, cobalt and its alloys, and mixtures thereof.

11. A method for the subcutaneous fixing of a catheter to a patient's body by means of the fixing system according to claim 1 which comprises: folding the base stop downwards along a folding axis, parallel to or coinciding with its longitudinal axis, so that the anchoring portions of the first and second arm are substantially aligned along an access axis; inserting only the anchoring portions in an access hole of a catheter operated on the skin of a patient; releasing the base stop so that the anchoring portions of the first and second arm are substantially divergent with respect to said access axis; lodging the catheter in the housing channel and securing the upper stop on the base stop.

* * * * *